(12) United States Patent
Wendell et al.

(10) Patent No.: US 12,061,870 B2
(45) Date of Patent: Aug. 13, 2024

(54) TECHNOLOGIES FOR RELATING TERMS AND ONTOLOGY CONCEPTS

(71) Applicant: tellic LLC, New York, NY (US)

(72) Inventors: Richard Edward Wendell, New York, NY (US); Eric Tanalski, Hillsborough, NJ (US); Christopher Russel Sipola, Brooklyn, NY (US); Michael Stanley, Skillman, NJ (US); Henry Edward Crosby, New York, NY (US); Loren Lee Chen, White Plains, NY (US); Paul Ton, New York, NY (US)

(73) Assignee: Tellic LLC, New York, NY (US)

( * ) Notice: Subject to any disclaimer, the term of this patent is extended or adjusted under 35 U.S.C. 154(b) by 274 days.

(21) Appl. No.: 17/776,999

(22) PCT Filed: Oct. 29, 2020

(86) PCT No.: PCT/US2020/057890
§ 371 (c)(1),
(2) Date: May 13, 2022

(87) PCT Pub. No.: WO2021/096690
PCT Pub. Date: May 20, 2021

(65) Prior Publication Data
US 2022/0398378 A1 Dec. 15, 2022

Related U.S. Application Data

(60) Provisional application No. 62/935,718, filed on Nov. 15, 2019.

(51) Int. Cl.
*G06F 40/295* (2020.01)
*G06F 16/31* (2019.01)
(Continued)

(52) U.S. Cl.
CPC ............ *G06F 40/247* (2020.01); *G06F 16/31* (2019.01); *G06F 16/3347* (2019.01); *G06F 40/295* (2020.01)

(58) Field of Classification Search
CPC ......... G06F 40/295; G06F 40/10; G06F 40/20
See application file for complete search history.

(56) References Cited

U.S. PATENT DOCUMENTS

2009/0182554 A1 7/2009 Abraham et al.
2011/0320459 A1* 12/2011 Chisholm ............... G06F 16/38
707/E17.084

(Continued)

FOREIGN PATENT DOCUMENTS

KR  20170133692  12/2017

OTHER PUBLICATIONS

International Search Report and Written Opinion dated Jan. 29, 2021 issued in corresponding PCT Application PCT/US20/57890 filed Oct. 29, 2020 (7 pages).

*Primary Examiner* — Daniel Abebe
(74) *Attorney, Agent, or Firm* — Dentons US LLP

(57) ABSTRACT

This disclosure enables various technologies that can (1) learn new synonyms for a given concept without manual curation techniques, (2) relate (e.g., map) some, many, most, or all raw named entity recognition outputs (e.g., "United States", "United States of America") to ontological concepts (e.g., ISO-3166 country code: "USA"), (3) account for false positives from a prior named entity recognition process, or (4) aggregate some, many, most, or all named entity recognition results from machine learning or rules based approaches to provide a best of breed hybrid approach (e.g., synergistic effect).

33 Claims, 6 Drawing Sheets

(51) Int. Cl.
*G06F 16/33* (2019.01)
*G06F 40/247* (2020.01)

(56) References Cited

U.S. PATENT DOCUMENTS

| | | | |
|---|---|---|---|
| 2012/0117082 A1* | 5/2012 | Koperda | G06F 16/24578 |
| | | | 707/E17.084 |
| 2013/0138696 A1 | 5/2013 | Turdakov et al. | |
| 2015/0081711 A1 | 3/2015 | Harris et al. | |
| 2017/0199963 A1* | 7/2017 | Kondadadi | G16H 15/00 |
| 2018/0082183 A1* | 3/2018 | Hertz | G06Q 10/10 |
| 2018/0232443 A1* | 8/2018 | Delgo | G06F 16/35 |

* cited by examiner

TECHNOLOGIES FOR RELATING TERMS AND ONTOLOGY CONCEPTS

CROSS-REFERENCE TO RELATED PATENT APPLICATION

This patent application claims the benefit of PCT International Application PCT/US20/57890 filed 29 Oct. 2020; which claims the benefit of U.S. Provisional Patent Application 62/935,718 filed 15 Nov. 2019; each of which is herein incorporated by reference for all purposes.

TECHNICAL FIELD

This disclosure relates to relating terms and ontology concepts.

BACKGROUND

Unstructured data sets present a unique challenge when trying to surface information. These data sets are typically documents, articles, emails and other written forms that can easily scale into billions of pages or other formats. While curating and indexing these documents is infeasible for humans at this scale, some scalable machine learning based approaches are able to handle this.

Some data curation pipelines generate meta-data from unstructured text. These processes extract key concepts, summaries, and usability metrics (e.g., relevance scores, confidence scores). The results are then typically fed into some downstream systems for power searching, index creation, and other similar tasks.

One component of data curation is a named entity recognition (NER) process. This process reads a document and then identifies one or more locations of a concept in the document. For example, the concept can include a category or type of term (e.g., person's full name, disease name, country name).

The NER process suffers from various technical problems. In particular, there may be multiple ways of conveying same thing (e.g., "USA" and "United States of America" as country names). As such, in order to have an effective index or search platform downstream, these terms would need to be linked as synonyms, which is computationally intensive, laborious, and time-consuming. This is further complicated by some concepts having standard preferred ontologies to which these concepts need to be mapped in order to be functional for downstream users. For example, a disease name "chronic obstructive pulmonary disease" should be converted to "Pulmonary Disease, Chronic Obstructive" if using a MeSH disease ontology. This is even further complicated by the NER process, whether dictionary or machine learning based, having an inherent false positive rate that passes bad results forward to downstream processes.

SUMMARY

Broadly, this disclosure enables various technologies that can (1) learn new synonyms for a given concept without manual curation techniques, (2) relate (e.g., map) some, many, most, or all raw NER outputs (e.g., "United States", "United States of America") to ontological concepts (e.g., ISO-3166 country code: "USA"), (3) account for false positives from a prior NER process, or (4) aggregate some, many, most, or all NER results from machine learning or rules based approaches to provide a best of breed hybrid approach (e.g., synergistic effect).

In an embodiment, a method comprises: reading, via a processor, an acronym entity extracted from an unstructured text; expanding, via the processor, the acronym entity such that a group of ontology candidate identifiers is generated; vectorizing, via the processor, the unstructured text such that a first output is generated, wherein the first output includes a plurality of words and a plurality of first relative weights, wherein the first relative weights correspond to the words, wherein the unstructured text contains the words; performing, via the processor, an entity mention vectorization on the acronym entity such that a second output is generated, wherein the second output includes a plurality of letter groups and a plurality of second relative weights, wherein the second relative weights correspond to the letter groups; selecting, via the processor, a member of the group of ontology candidate identifiers based on the first words, the first relative weights, the letter groups, and the second relative weights; generating, via the processor, a confidence score for the member; determining, via the processor, whether the acronym entity is a false positive based on the first output, the second output, and the confidence score; and writing, via the processor, the member and the confidence score into an index based on the acronym entity not being the false positive such that the member is associated with the confidence score in the index, wherein the index refers to the unstructured text based on the member.

In an embodiment, a method comprises: reading, via a processor, a hyphenated entity extracted from an unstructured text; performing, via the processor, a string match on the hyphenated entity such that an ontology candidate identifier is generated; vectorizing, via the processor, the unstructured text such that a first output is generated, wherein the first output includes a plurality of words and a plurality of first relative weights, wherein the first relative weights correspond to the words, wherein the unstructured text contains the words; performing, via the processor, an entity mention vectorization on the hyphenated entity such that a second output is generated, wherein the second output includes a plurality of letter groups and a plurality of second relative weights, wherein the second relative weights correspond to the letter groups; selecting, via the processor, the ontology candidate identifier based on the first words, the first relative weights, the letter groups, and the second relative weights; generating, via the processor, a confidence score for the ontology candidate identifier; determining, via the processor, whether the hyphenated entity is a false positive based on the first output, the second output, and the confidence score; and writing, via the processor, the ontology candidate identifier and the confidence score into an index based on the hyphenated entity not being the false positive such that the ontology candidate identifier is associated with the confidence score in the index, wherein the index refers to the unstructured text based on the ontology candidate identifier.

In an embodiment, a method comprises: reading, via a processor, an entity extracted from an unstructured text; performing, via the processor, an ontology-specific screen on the entity such that an ontology candidate identifier is generated; vectorizing, via the processor, the unstructured text such that a first output is generated, wherein the first output includes a plurality of words and a plurality of first relative weights, wherein the first relative weights correspond to the words, wherein the unstructured text contains the words; performing, via the processor, an entity mention vectorization on the entity such that a second output is generated, wherein the second output includes a plurality of letter groups and a plurality of second relative weights, wherein the second relative weights correspond to the letter groups; selecting, via the processor, the ontology candidate identifier based on the first words, the first relative weights, the letter groups, and the second relative weights; generating, via the processor, a confidence score for the ontology candidate identifier; determining, via the processor, whether the entity is a false positive based on the first output, the second output, and the confidence score; and writing, via the processor, the ontology candidate identifier and the confidence score into an index based on the entity not being the false positive such that the ontology candidate identifier is associated with the confidence score in the index, wherein the index refers to the unstructured text based on the ontology candidate identifier.

DETAILED DESCRIPTION OF PREFERRED EMBODIMENTS

Figure 1:
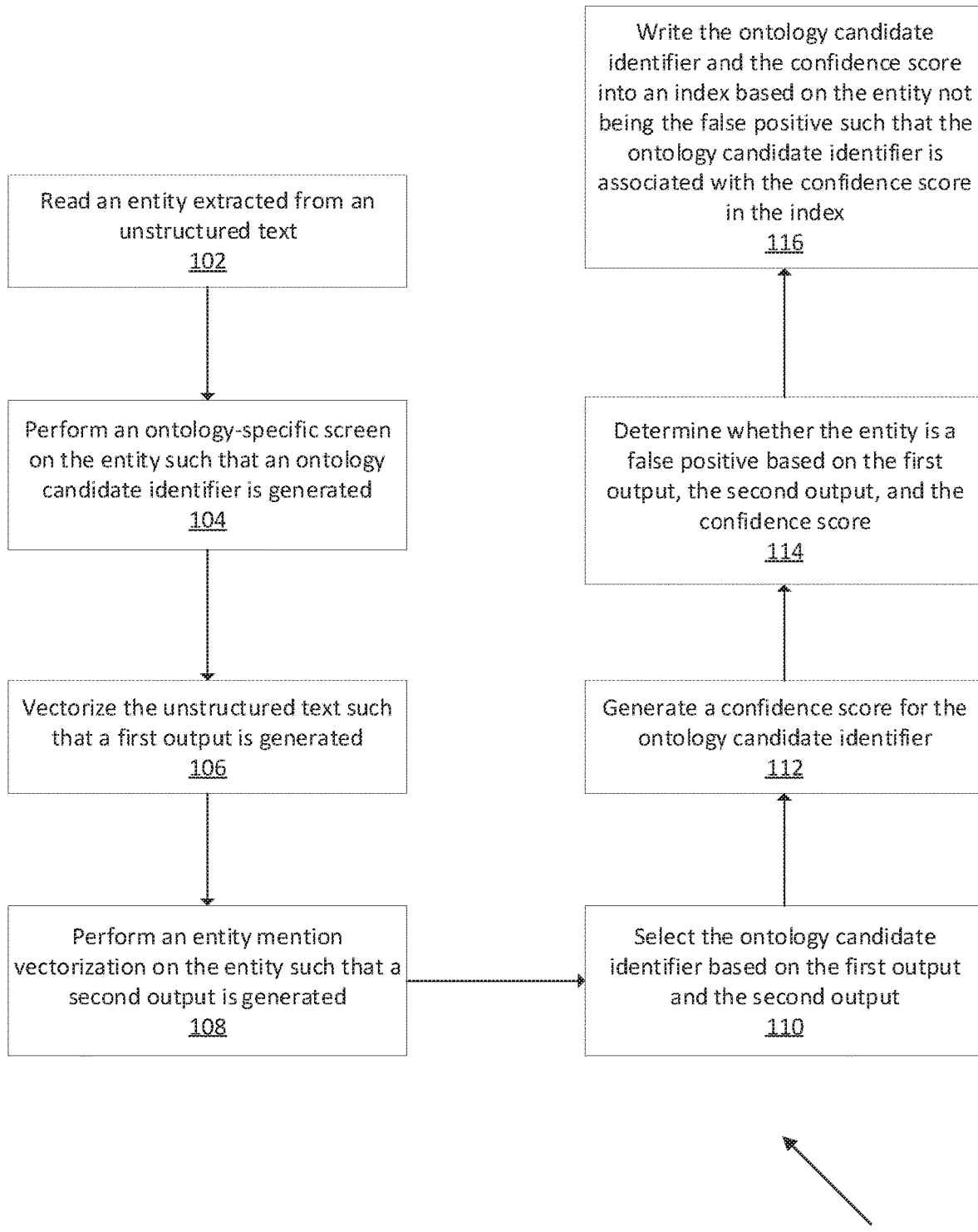
FIG. 1 shows a flowchart of an embodiment of a method for modifying an index according to this disclosure.

Broadly, this disclosure enables various technologies that can (1) learn new synonyms for a given concept without manual curation techniques, (2) relate (e.g., map) some, many, most, or all raw NER outputs (e.g., "United States", "United States of America") to ontological concepts (e.g., ISO-3166 country code: "USA"), (3) account for false positives from a prior NER process, or (4) aggregate some, many, most, or all NER results from machine learning or rules based approaches to provide a best of breed hybrid approach (e.g., synergistic effect).

For example, a computing process, as disclosed herein, can take in words or phrases that are identified as entity mentions in a raw source document and map (or otherwise relates) these words or phrases to a selected ontology (or vice versa). Some, many, most, or all incoming words/phrases can be outputs of a NER process or dictionary search. An entity can be a mention of a type of term found in the text (e.g., a person's full name, nickname, or identifier, a company name, nickname, or identifier, a geographic location name, nickname, or identifier, a disease name, nickname, or identifier, a gene name, nickname, or identifier, an item of interest name, nickname, or identifier). The entity can be a raw text as that raw text appears in a text source. The computing process can map (or otherwise relate) the entity to a location in a selected ontology (or vice versa). When the computing process is run across various data sets, then the computing process can generate deeper synonym lists for some, many, most, or all ontological concept than are available through manual curation means. The computing process can accommodate and detect false positives in a NER process. The computing process can be used to create a hybrid solution that combines multiple NER approaches (e.g., machine learning, dictionary, rules-based dictionary) and creates a singular output that outperforms any of such approaches individually (e.g., synergistic effect).

For example, the computing process can run on computer systems, servers (e.g., physical, virtual, application) and cloud-based environments (e.g., public, private), while assuming that (1) some, many, most, or all unstructured documents have been converted into some electronic text form (e.g., file format that uses human-readable text to transmit data objects consisting of attribute-value pairs and array data types, JavaScript object notation (JSON) file, extensible markup language (XML) file, text file, database table, data structure, array) and (2) a NER process has created a list of entity locations in a form of start and end characters (e.g., alphabetic, numeric) for some, many, most, or all entity references in some, many, most, or all documents.

The process includes an input inclusive of a plurality of data sources (e.g., static, dynamic). For example, the data sources can include unstructured source documents in electronic text format (e.g., text file, email file, markup file, descriptive text). The data sources can include extracted entities with their locations in documents indexed at character level. The data sources can include an ontology synonym list stored electronically. The ontology synonym list can include key concepts, a preferred name for those concepts, a set of synonyms for those concepts, or a parent-child hierarchy. The data sources can include a set of pre-computed vectors for the ontology concepts and synonyms (e.g., document vectors for some, many, most, or all concepts, character vectors for some, many, most, or all synonyms. The data sources can include a definition of a screen (or filtering) order for candidate generation. The data sources can include an acronym expansion reference. The data sources can include a threshold for an upper bound of an n-gram size. The data sources can include a flag to specify a number of workers (e.g., process thread) to use. The data sources can include a document vector definition file. The data sources can include a vectorizer method flag (or another semaphore). The data sources can include a cutoff for a candidate selection score (e.g., score below threshold means no or low likelihood of match). The data sources can include a parameter for a relative weight of document context when compared to a weight of entity mention.

For example, when the computing process begins (which can be within another process), a computing logic (e.g., module, function, library) determines if the computing logic is running in a single-worker or master/slave mode depending on a computing platform configuration detected (e.g., automatically take advantage of cloud environments) or various input flag values. For master/slave mode, some, many, most, or all documents are batched (or otherwise organized or grouped) to distribute evenly (or unevenly based on certain distribution algorithms) across some, many, most, or all workers. Some, many, most, or all workers can contain a copy of some, many, most, or all relevant code libraries. Some, many, most, or all works can independently processes some, many, most, or all documents in series (or in parallel). Some, many, most, or all workers can aggregate some, many, most, or all results and return these results to a master node in form structured electronic documents. Some of resulting data can be saved to disk, written to a database table, saved in a document indexing system, or passed in-memory to subsequent processing methods.

This disclosure is now described more fully with reference to FIGS. 1-4B, in which some embodiments of this disclosure are shown. This disclosure may, however, be embodied in many different forms and should not be construed as necessarily being limited to the embodiments disclosed herein. Rather, these embodiments are provided so that this disclosure is thorough and complete, and fully conveys various concepts of this disclosure to skilled artisans.

Various terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

The terminology used herein is for describing particular example embodiments and is not intended to be necessarily limiting of the present disclosure. As used herein, the singular forms "a," "an" and "the" are intended to include the plural forms (e.g., two, three, four, five, six, seven, eight, nine, ten, tens, hundreds, thousands, millions) as well, unless the context clearly indicates otherwise. Also, as used herein, the term "a" and/or "an" shall mean "one or more," even though the phrase "one or more" is also used herein. The terms "comprises," "includes" and/or "comprising," "including" when used in this specification, specify the presence of stated features, integers, steps, operations, elements, and/or components, but do not preclude the presence and/or addition of one or more other features, integers, steps, operations, elements, components, and/or groups thereof. Furthermore, when the present disclosure states herein that something is "based on" something else, then such statement refers to a basis which may be based on one or more other things as well. In other words, unless expressly indicated otherwise, as used herein "based on" inclusively means "based at least in part on" or "based at least partially on." Additionally, as used herein, a term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances.

FIG. 1 shows a flowchart of an embodiment of a method for modifying an index according to this disclosure. In particular, a method 100 includes a plurality of blocks 102-116, which are processor-executed.

In block 102, a processor reads an entity extracted from an unstructured text, as disclosed herein. The entity can be an acronym entity, a hyphenated entity, or another entity. The acronym entity or the hyphenated entity can be extracted from the unstructured text via a NER process. For example, the unstructured text can include a descriptive text.

The entity can be an acronym entity expanded based on an ontology-specific dataset. The entity can be an acronym entity expanded based on the acronym entity matching an acronym in an ontology-specific dataset.

The entity can be a hyphenated entity string matched based on an ontology-specific dataset. The entity can be a hyphenated entity that is string matched based on the hyphenated entity having a lowercase match in the ontology-specific dataset.

The entity can include a Greek letter or a Roman numeral. The entity can have a high token vector cosine similarity to an ontology concept, where the ontology candidate identifier and the ontology concept are associated with an ontology. Note that the entity can be at least two, three, or more of an acronym entity, a hyphenated entity, an entity including a Greek letter, an entity that includes a Roman numeral, or an entity that has a high token vector cosine similarity to an ontology concept, where the ontology candidate identifier and the ontology concept are associated with an ontology.

In block 104, the processor performs an ontology-specific screen on the entity such that an ontology candidate identifier is generated, as disclosed herein. For example, the ontology candidate identifier can be a MeSH identifier (or other ontology candidate identifiers). For example, the entity can be a hyphenated entity that is string matched such that the ontology candidate identifier is generated. For example, the processor can expand the acronym entity such that a group of ontology candidate identifiers is generated. For example, a member of a group of candidate identifiers can be selected based on at least one of a pattern or an inference learned from a dataset prior to an acronym entity being read.

There can be a plurality of ontology-specific screens. For example, the ontology-specific screen can include at least one of an exact match, an acronym expansion, or a lowercase match. For example, if the ontology-specific screen is a first ontology-specific screen, then the lowercase match can precede a second ontology-specific screen other than the exact match and the acronym expansion. For example, the exact match can precede the acronym expansion. For example, the exact match can precede the lowercase match. For example, the acronym expansion can precede the lowercase match. For example, the acronym expansion can occur after the exact match and before the lowercase match. For example, the acronym expansion can immediately follow the exact match. For example, the lowercase match can immediately follow the acronym expansion. For example, at least one of the exact match or the acronym expansion precede another ontology-specific screen other than the lowercase match. For example, the exact match can precede another ontology-specific screen. For example, the acronym expansion can precedes another ontology-specific screen.

The ontology candidate identifier can be a member of a group of ontology candidate identifiers, where the member of the group of candidate identifiers can be selected based on at least one of a pattern or an inference learned from a dataset prior to the entity being read. The entity can be an acronym entity that is expanded such that the group of ontology candidate identifiers is generated. For example, a member of the group of candidate identifiers can be a MeSH identifier.

The ontology candidate identifier can be a member of a group of ontology candidate identifiers. The group of candidate identifiers can be sourced from at least one of a group of Medical Subject Heading (MeSH) identifiers, a group of Monarch Disease Ontology (MONDO) identifiers, a group of Disease Ontology (DO) identifiers, a group of Experimental Factor Ontology (EFO) identifiers, a group of INTERNATIONAL CLASSIFICATION OF DISEASES, NINTH EDITION (ICD9) identifiers, a group of INTERNATIONAL CLASSIFICATION OF DISEASES, TENTH EDITION (ICD10) identifiers, a group of Comparitive Toxicogenomics Database (CTD)'s MEDIC disease vocabulary identifiers, a group of SNOMED CT identifiers, a group of the National Center for Biotechnology Information (NCBI)'s Gene Entrez identifiers, a group of Ensembl Gene ID identifiers, a group of Uniprot identifiers, a group of Gene Ontology (GO) identifiers, a group of Protein Ontology identifiers, a group of HUGO GENE NOMENCLATURE COMMITTEE (HGNC)'S identifiers, a group of PFAM identifiers, a group of University of California Santa Cruz (UCSC) Genome identifiers, a group of Panther identifiers, a group of Kyoto Encyclopedia of Genes and Genomes (KEGG) identifiers, a group of National Center for Biotechnology Information (NCBI) Taxonomy identifiers, a group of Biological Assay Ontology (BAO) identifiers, a group of Human Phenotype Ontology (HPO) identifiers, a group of Mammalian Phenotype Ontology (MPO) identifiers, a group of ONLINE MENDELIAN INHERITANCE IN MAN(O-MIM)'S identifiers, a group of Phenotype & Trait Ontology identifiers, a group of Cell Ontology (CL) identifiers, a group of Cell Line Ontology (CLO) identifiers, a group of Cellosaurus identifiers, a group of Gene Ontology (GO) identifiers, a group of Pathway Ontology identifiers, a group of Reactome identifiers, a group of Kyoto Encyclopedia of Genes and Genomes (KEGG)'s identifiers, a group of ConsensusPathDB identifiers, a group of ChemBL identifiers, a group of IUPAC identifiers, a group of ChEBI identifiers, a group of Chem INF identifiers, a group of FDA NATIONAL DRUG CODE (NDC) identifiers, a group of International Nonproprietary Name (INN) identifiers, a group of United States Adopted Name (USAN) identifiers, a group of Food and Drug Administration (FDA) Purple Book identifiers, a group of FDA Orange Book identifiers, a group of INTERNATIONAL UNION OF BIOCHEMISTRY AND MOLECULAR BIOLOGY (IUBMB) identifiers, a group of BRENDA identifiers, a group of dbSNP identifiers, a group of SNPedia identifiers, a group of THE AMERICAN MEDICAL ASSOCIATION'S CURRENT PROCEDURAL TERMINOLOGY(CPT) identifiers, a group of THE REGENSTRIEF INSTITUTE'S LOGICAL OBSERVATION IDENTIFIERS NAMES AND CODES (LOINC) identifiers, a group of Units of Measurement Ontology (UO) identifiers, a group of International Standards Organization (ISO) 3116-1 identifiers, a group of ISO 3116-2 identifiers, or a group of Geographic Entity Ontology (GEO) identifiers. The group of candidate identifiers can be sourced from a group of non-medical or non-life science identifiers, such as included in an AURUM—Information Security Ontology, Basic Formal Ontology, e-Business Model Ontology, CContology (Customer Complaint Ontology), General Automotive Ontology, OMNIBUS Ontology, CIDOC Conceptual Reference Model, Gellish English dictionary, FAO geopolitical ontology, UMBEL (Upper Mapping and Binding Exchange Layer) ontology, IDEAS (International Defense Enterprise Architecture Specification) ontology, or others.

The ontology candidate identifier can be sourced from at least one of a group of Medical Subject Heading (MeSH) identifiers, a group of Monarch Disease Ontology (MONDO) identifiers, a group of Disease Ontology (DO) identifiers, a group of Experimental Factor Ontology (EFO) identifiers, a group of INTERNATIONAL CLASSIFICATION OF DISEASES, NINTH EDITION (ICD9) identifiers, a group of INTERNATIONAL CLASSIFICATION OF DISEASES, TENTH EDITION (ICD10) identifiers, a group of Comparitive Toxicogenomics Database (CTD)'s MEDIC disease vocabulary identifiers, a group of SNOMED CT identifiers, a group of the National Center for Biotechnology Information (NCBI)'s Gene Entrez identifiers, a group of Ensembl Gene ID identifiers, a group of Uniprot identifiers, a group of Gene Ontology (GO) identifiers, a group of Protein Ontology identifiers, a group of HUGO GENE NOMENCLATURE COMMITTEE (HGNC)'S identifiers, a group of PFAM identifiers, a group of University of California Santa Cruz (UCSC) Genome identifiers, a group of Panther identifiers, a group of Kyoto Encyclopedia of Genes and Genomes (KEGG) identifiers, a group of National Center for Biotechnology Information (NCBI) Taxonomy identifiers, a group of Biological Assay Ontology (BAO) identifiers, a group of Human Phenotype Ontology (HPO) identifiers, a group of Mammalian Phenotype Ontology (MPO) identifiers, a group of ONLINE MENDELIAN INHERITANCE IN MAN(OMIM)'S identifiers, a group of Phenotype & Trait Ontology identifiers, a group of Cell Ontology (CL) identifiers, a group of Cell Line Ontology (CLO) identifiers, a group of Cellosaurus identifiers, a group of Gene Ontology (GO) identifiers, a group of Pathway Ontology identifiers, a group of Reactome identifiers, a group of Kyoto Encyclopedia of Genes and Genomes (KEGG)'s identifiers, a group of ConsensusPathDB identifiers, a group of ChemBL identifiers, a group of IUPAC identifiers, a group of ChEBI identifiers, a group of Chem INF identifiers, a group of FDA NATIONAL DRUG CODE (NDC) identifiers, a group of International Nonproprietary Name (INN) identifiers, a group of United States Adopted Name (USAN) identifiers, a group of Food and Drug Administration (FDA) Purple Book identifiers, a group of FDA Orange Book identifiers, a group of INTERNATIONAL UNION OF BIOCHEMISTRY AND MOLECULAR BIOLOGY (IUBMB) identifiers, a group of BRENDA identifiers, a group of dbSNP identifiers, a group of SNPedia identifiers, a group of THE AMERICAN MEDICAL ASSOCIATION'S CURRENT PROCEDURAL TERMINOLOGY(CPT) identifiers, a group of THE REGENSTRIEF INSTITUTE'S LOGICAL OBSERVATION IDENTIFIERS NAMES AND CODES (LOINC) identifiers, a group of Units of Measurement Ontology (UO) identifiers, a group of International Standards Organization (ISO) 3116-1 identifiers, a group of ISO 3116-2 identifiers, or a group of Geographic Entity Ontology (GEO) identifiers. The ontology candidate identifier can be sourced from a group of non-medical or non-life science identifiers, such as included in an AURUM—Information Security Ontology, Basic Formal Ontology, e-Business Model Ontology, CContology (Customer Complaint Ontology), General Automotive Ontology, OMNIBUS Ontology, CIDOC Conceptual Reference Model, Gellish English dictionary, FAO geopolitical ontology, UMBEL (Upper Mapping and Binding Exchange Layer) ontology, IDEAS (International Defense Enterprise Architecture Specification) ontology, or others.

In certain embodiments, the ontology candidate identifier can be a member of a group of identifiers used in a particular field, such as engineering, electronics, automotive, energy, security, transportation, manufacturing, finance, law, advertising, science, real estate, telecommunications, military, government, or other domains of discourse or domain-specific ontologies.

In certain embodiments, the ontology candidate identifier can be a member of a group of identifiers used in a particular language, such as English, French, Spanish, Mandarin, Cantonese, Japanese, Korean, Russian, Arabic, Hebrew, Hindu, Urdu, Bengali, or any other language. For example, the identifiers can be reviewed from left to right, from right to left, from top to bottom, from bottom to top, or in a any other direction.

In block 106, the processor vectorizes the unstructured text such that a first output (e.g., alphanumeric data) can be generated, as disclosed herein. The first output can include a plurality of words, symbols, or characters, or any combination of the foregoing, and a plurality of first relative weights. The first relative weights can correspond to the words, symbols, and/or characters (e.g., one-to-one correspondence). The unstructured text can contain the words, symbols, and/or characters.

In block 108, the processor performs an entity mention vectorization on the entity such that a second output (e.g., alphanumeric data) can be generated, as disclosed herein. The second output can include a plurality of letter, symbol, and/or character groups and a plurality of second relative weights. The second relative weights can correspond to the letter, symbol, and/or character groups (e.g., one-to-one correspondence).

In block 110, the processor selects the ontology candidate identifier based on the first words, symbols, and/or characters, the first relative weights, the letter, symbol, and/or character groups, and the second relative weights, as disclosed herein. For example, when the entity is an acronym entity, the processor can select a member of a group of ontology candidate identifiers (formed from expanding acronym entity) based on the first words, symbols, and/or characters, the first relative weights, the letter, symbol, and/or character groups, and the second relative weights.

In block 112, the processor generates a confidence score for the ontology candidate identifier, as disclosed herein.

In block 114, the processor determines whether the entity is a false positive based on the first output, the second output, and the confidence score, as disclosed herein. Note that the false positive can also be indicated by testing for not being a true positive.

In block 116, the processor writes the ontology candidate identifier and the confidence score into an index based on the entity not being the false positive such that the ontology candidate identifier is associated with the confidence score in the index, as disclosed herein. The index can refer to the unstructured text based on the ontology candidate identifier. For example, when the entity is an acronym entity, the index refers to the unstructured text based on a member of a group of ontology candidate identifiers (formed from expanding acronym entity) selected based on the first words, symbols, and/or characters, the first relative weights, the letter, symbol, and/or character groups, and the second relative weights.

Note that the processor can run a thread performing at least two, three, four or more of performing the ontology-specific screen (e.g., expanding acronym entity), vectorising the unstructured text, symbols, and/or characters, performing the entity mention vectorization, selecting the ontology candidate identifier (e.g., selecting member of group of candidate identifiers), generating the confidence score, determining whether the entity is the false positive, or writing the ontology candidate identifier and the confidence score into the index.

Note that other forms of action other than writing are possible, where these forms of action involve the ontology candidate identifier or the confidence score. Some of such forms of action can include requesting an input device to generate an input, requesting an output device to generate an output, modifying a data structure other than the index, deleting a data structure, creating a data structure, sorting a data structure, searching a data structure, calling a library, generating a computing event, or other forms of action.

Figure 2:
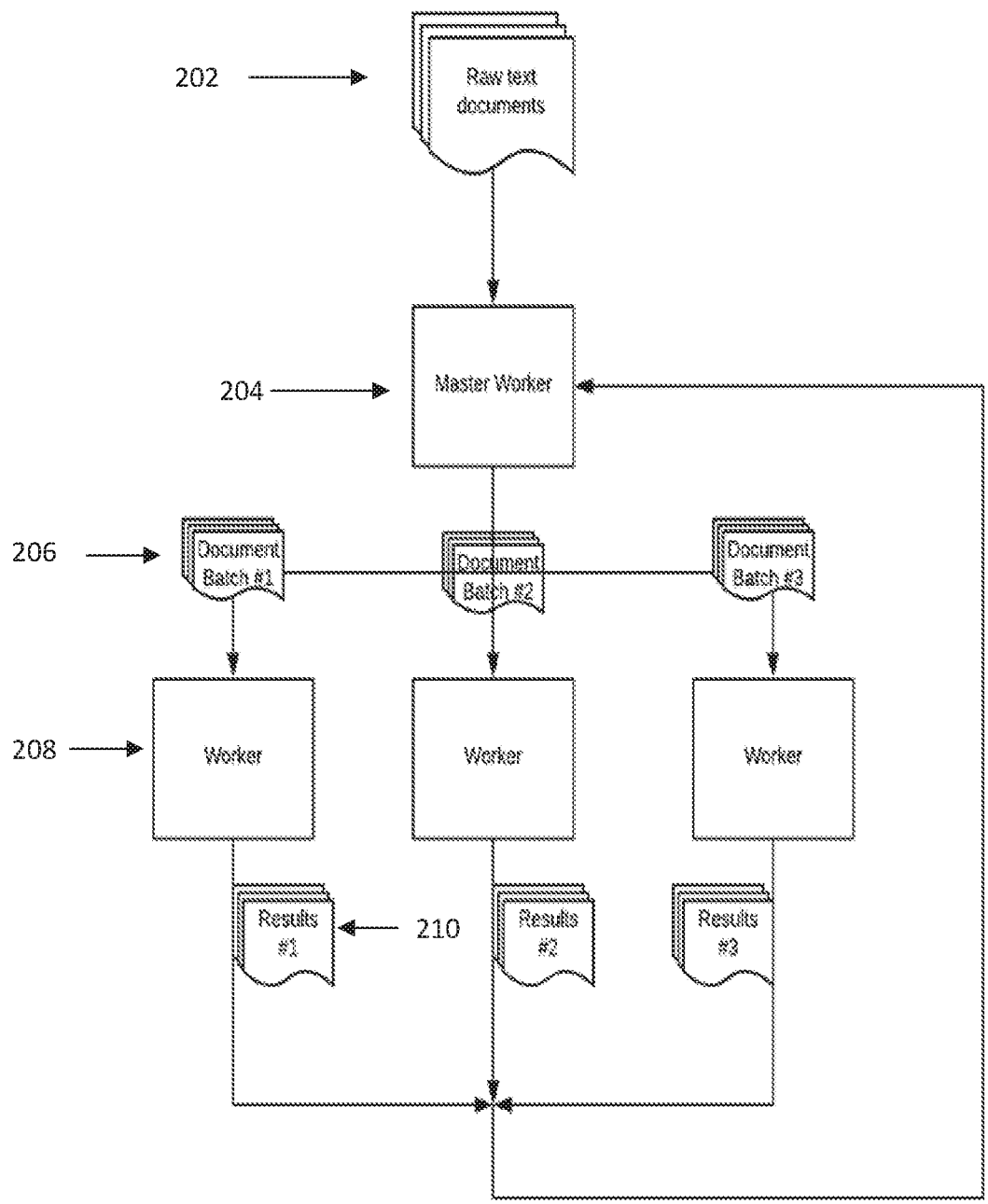
FIG. 2 shows a flow diagram of an embodiment of a system for document processing according to this disclosure.

FIG. 2 shows a flow diagram of an embodiment of a system for document processing according to this disclosure. In particular, a system 200 includes a plurality of logical blocks 202-210. Block 202 represents various raw text documents (e.g., files, emails, web pages, text files, descriptive text). Block 204 represents a master worker (e.g., master processing thread). Block 206 represents a plurality of document batches (or groups). Block 208 represents a plurality of workers (e.g., processing threads) controlled by the block 204. Block 210 represents a plurality of result groups (e.g., one-to-one correspondence, one-to-many correspondence, many-to-many correspondence, many-to-one correspondence) output by the blocks 208.

For example, the block 204 (master worker) can read (or is sent) a plurality of entities extracted from a plurality of unstructured text sources of blocks 202 (raw text documents). The block 204 distributes workload (processing resulting from reading entities or accessing entities) across the blocks 206. Then, the blocks 208 (workers) (1) perform an ontology-specific screen(s) on the entities such that a plurality of ontology candidate identifiers is generated and (2) vectorize the unstructured text such that a first output is generated, where the first output includes a plurality of words and a plurality of first relative weights and where the first relative weights correspond to the words, wherein the unstructured text contains the words. Then, the blocks 208 (1) perform an entity mention vectorization on the entities such that a second output is generated, where the second output includes a plurality of letter groups and a plurality of second relative weights and where the second relative weights correspond to the letter groups. Then, the blocks 208 (1) select the ontology candidate identifiers based on the first words, the first relative weights, the letter groups, and the second relative weights, (2) generate a plurality of confidence scores for the ontology candidate identifiers, and (3) determine whether the entities are a false positive based on the first output, the second output, and the confidence scores. Then, the blocks 208 output the blocks 210 (results) and the block 210 can then be merged and iteratively fed back to the block 204. Then, the block 204 can write the ontology candidate identifiers and the confidence scores into an index based on the entities not being the false positive such that the ontology candidate identifiers are is associated with the confidence scores in the index, where the index refers to the unstructured text based on the ontology candidate identifiers.

Figure 3A:
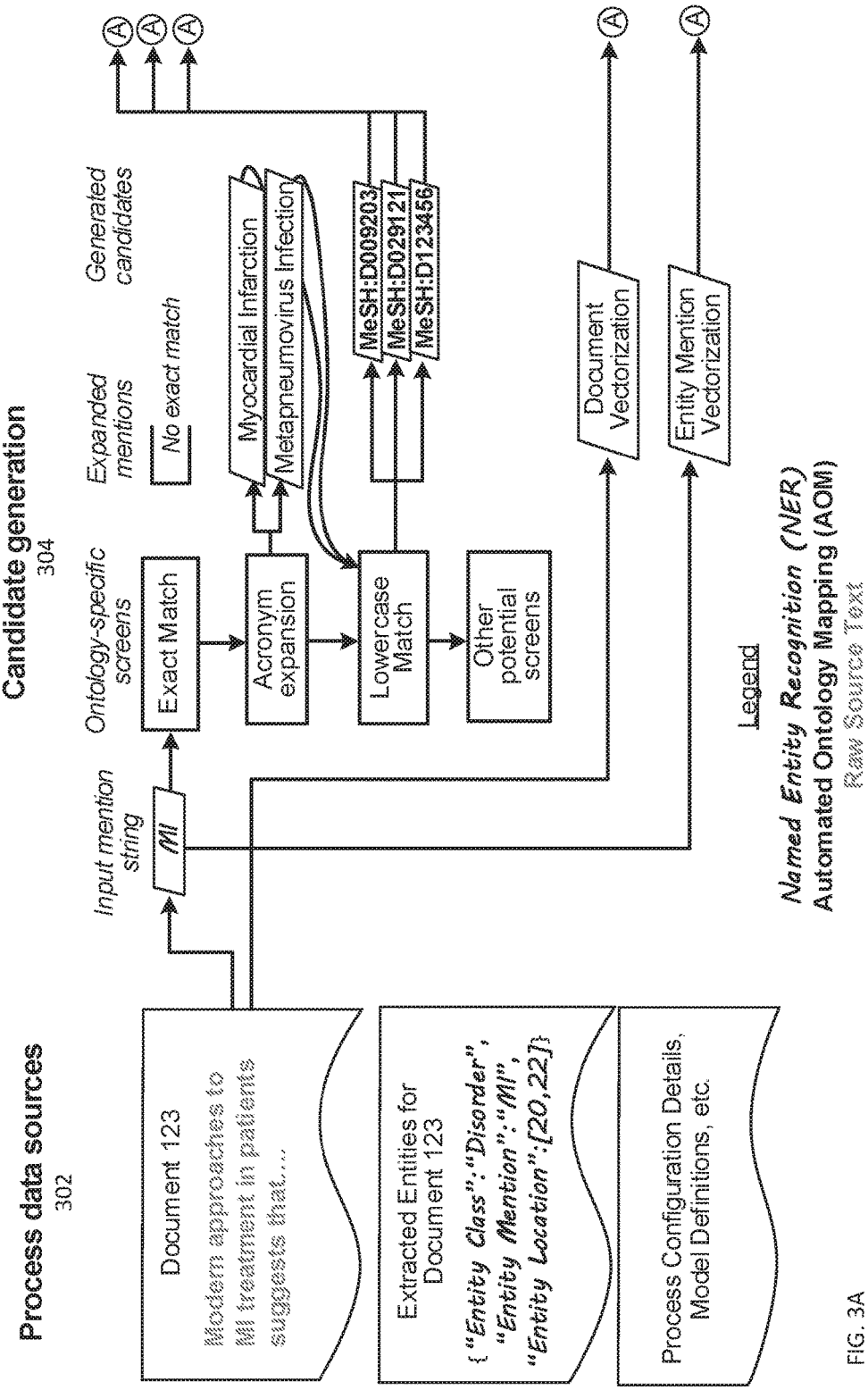
FIGS. 3A and 3B shows a flowchart of an embodiment of a method for modifying an index based on an acronym expansion according to this disclosure.
Figure 3B:
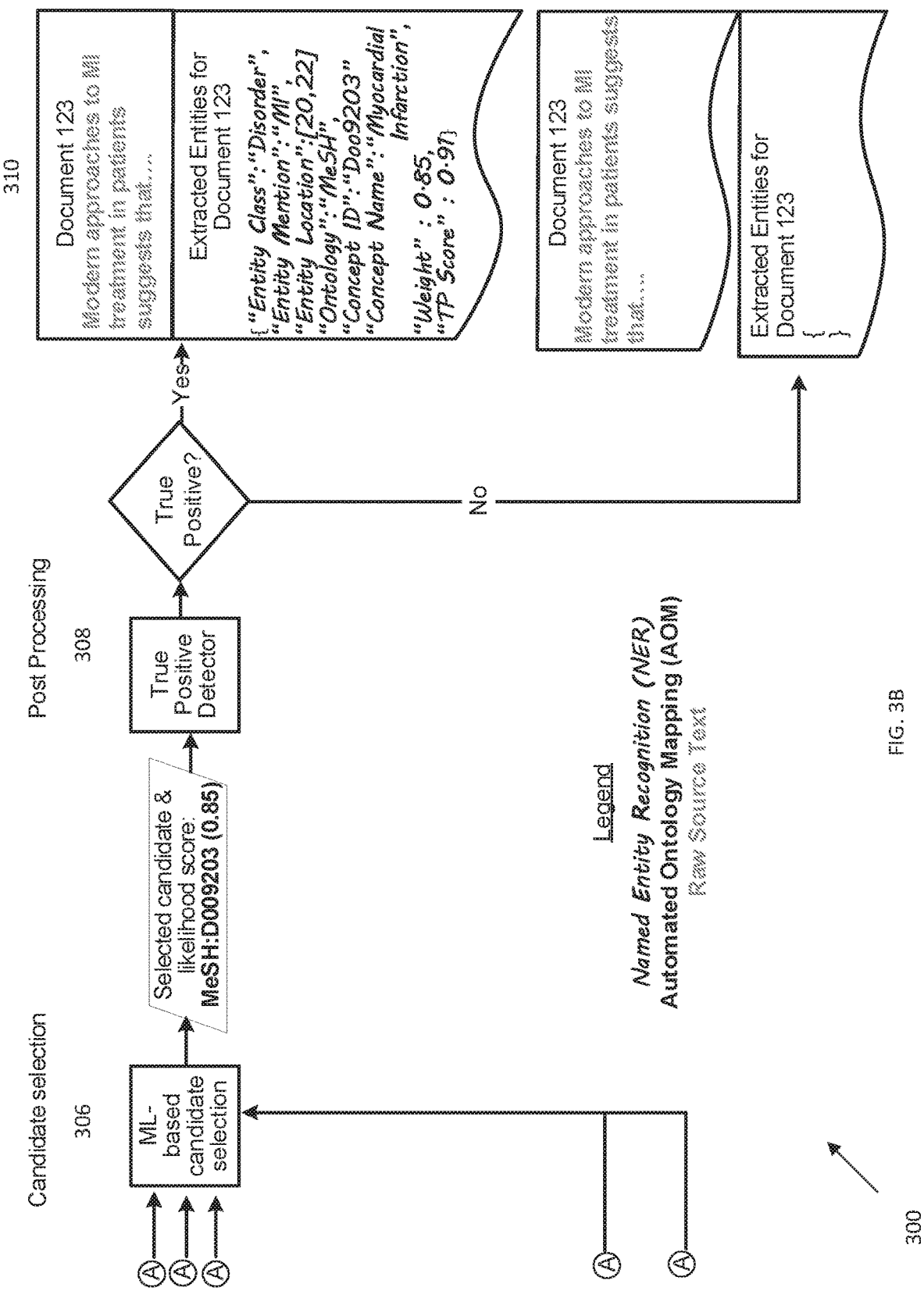
Figure 4A:
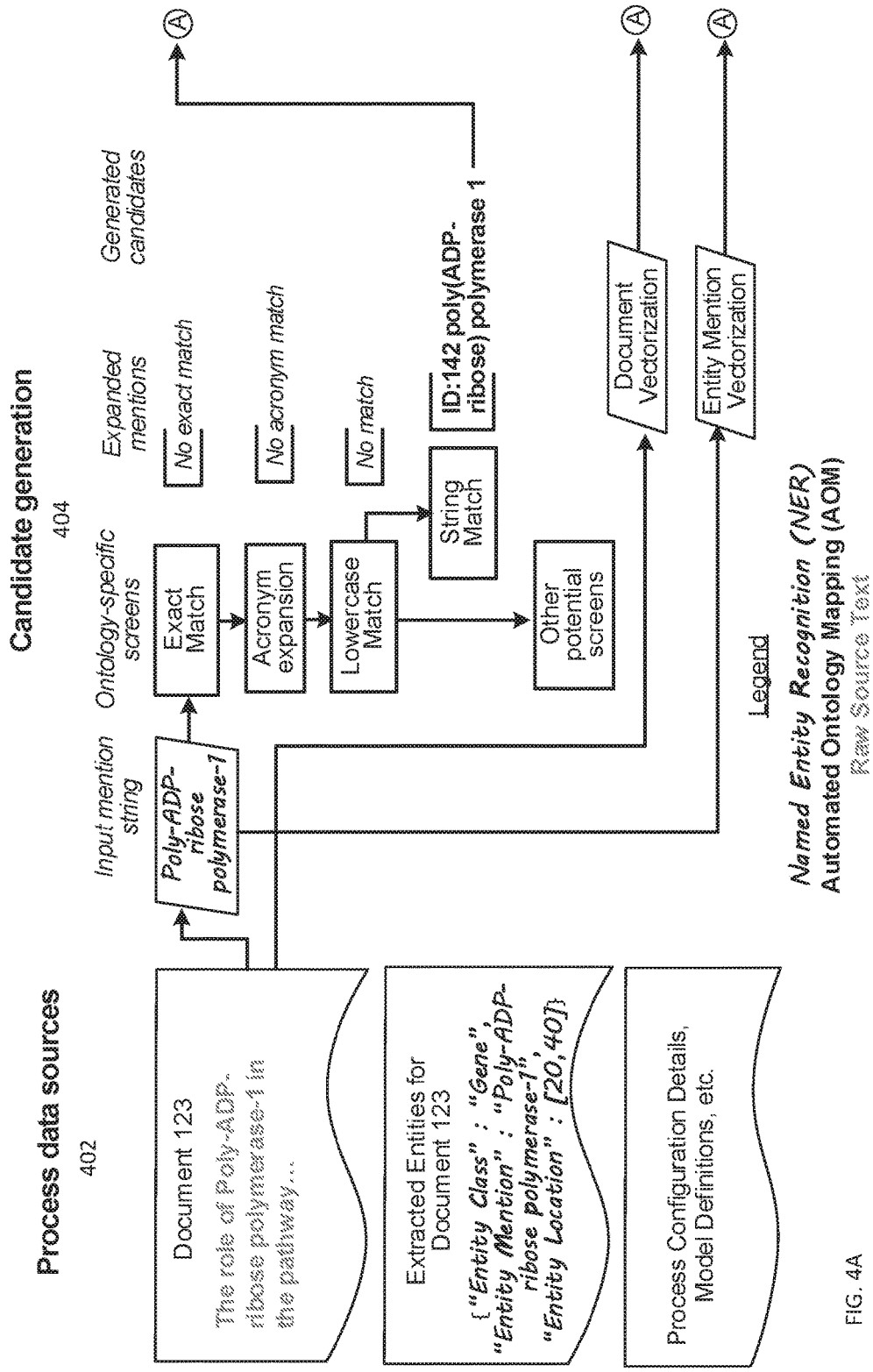
FIGS. 4A and 4B shows a flowchart of an embodiment of a method for modifying an index based on a string match according to this disclosure.
Figure 4B:
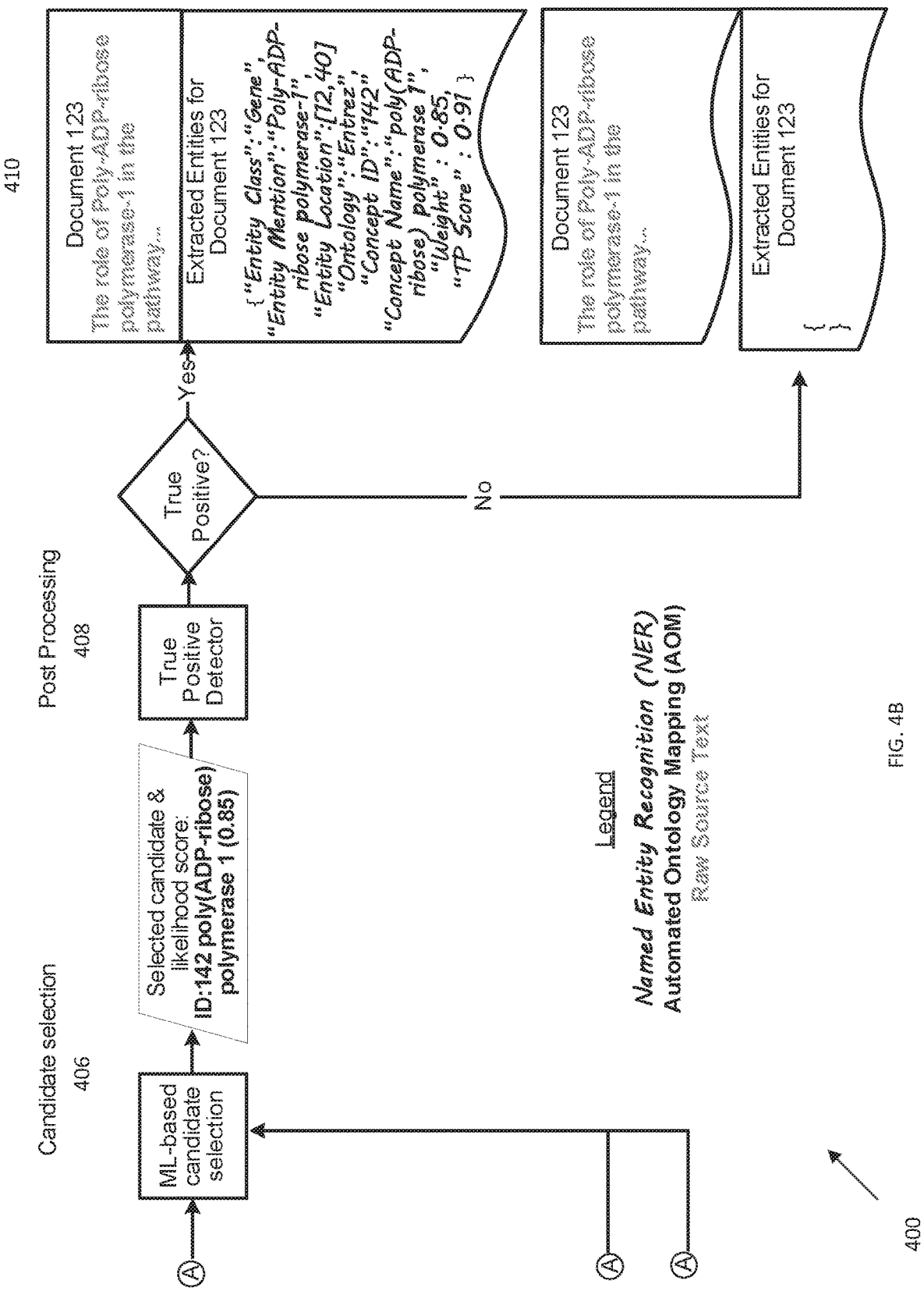

FIGS. 3A and 3B shows a flowchart of an embodiment of a method for modifying an index based on an acronym expansion according to this disclosure. FIGS. 4A and 4B shows a flowchart of an embodiment of a method for modifying an index based on a string match according to this disclosure. Before these flowcharts are further explained, several concepts are further explained.

An ontology mapping process within an individual worker (e.g., processing thread) can include some raw ontology files and other data being read into a memory (e.g., random access memory, processor cache). If not already resident in the memory, then document source file(s) can be loaded into the memory. Various entity mentions that match various selected entity types can be extracted by searching for matching entity types. Full source text can then be vectorized (see Example 2 below) and document can be broken down into words/sentences using standard natural language processing (NLP) tools (e.g., tokenization, lemmatization, stemming). Stop words, i.e., common (uninformative) words, can be identified via dictionary lookup and removed from corpus. Single terms can be combined into n-grams (i.e. n-term phrases) for a predefined upper limit of n. N-grams with a low rate of occurrence can be removed from list and a document vector definition can be loaded into the memory. Document content can be vectorized and projected against a loaded vector via at least one of a term-frequency weighting (e.g., term frequency-inverse document frequency (TF-IDF) through standard tools or scikit-learn truncated singular value decomposition (SVD) methods or others) or a machine-learning based approach (e.g., Bidirectional Encoder Representations from Transformers (BERT), NLP tool for representing documents as vector, Doc2vec). For some, many, most, or all entities explained above (e.g., various entity mentions that match selected entity type), there can be ran an ontology mapping process explained below. At least some output of this process can be saved in a JSON dictionary structure (or another data format e.g., markup language data structure, XML). For some, many, most, or all entities, at least some of following information can be captured: a selected ontology, an identifier for a matched location in the selected ontology, a preferred name for the matched location in the selected ontology, an overall weight of the matched location, a calculated score from an intermediate step in this process.

An ontology mapping process for a single entity can include a candidate generation technique that maps an incoming entity term to several potential ontology entry matches. Based upon an ontology screen order and configuration, as explained above, this process takes in an entity mention and generates a set of potential ontology matches using various screens. For example, a screen can be a pass-all screen where an entire ontology synonym list is added to a candidate list (see Example 4 below). For example, a screen can be a string match screen an entry in an ontology synonym list that is a match to an entity term is added to a candidate list, where the entity mention and ontology strings can be pre-processed by removing punctuation (see Example 5 below). For example, a screen can be a fuzzy match screen where an entry in an ontology synonym list that is within a fixed distance based upon various fuzzy string matching methods (e.g., Levenshtein Distance, Hamming Distance, Euclidean Distance, Damerau-Levenshtein Distance, Sellers Distance). For example, a screen can be an acronym mention screen where some, many, most, or all known acronyms can be replaced with their full strings and vice versa. The output strings can be added to a candidate list. For example, a screen can be a Greek-to-Roman character substitution: map Greek letters (e.g., "a") to their Roman alphabet spelling (e.g., "alpha"). For example, a screen can be Roman Numeral conversion: convert Roman numerals (e.g., "IV") into their corresponding Arabic numerals (e.g., 4). For example, a screen can be a Token Vector Similarity: a matching process based upon a cosine similarity of a token/n-gram vector (see Example 3 below). The cosine similarity between the entity mention vector, $A_i$, and the ontology synonym vector, $B_i$, can be defined as:

$$\text{Similarity} = \frac{\sum_i A_i \cdot B_i}{\left(\sum_i A_i^2 \cdot \sum_i B_i^2\right)^{0.5}}$$

The two tokens or n-grams can be considered sufficiently similar if the similarity score is greater than a pre-defined threshold provided in the process input. For example, a screen can be a partial match ontology screen for checking to see if the entity mention is a token-wise substring of the ontology (see Example 6 below). For example, the screen can be a partial match entity screen for checking to see if the ontology mention is a token-wise substring of the entity (see Example 7 below).

Some screens may take additional data and parameters. The acronym mention screen can take a mapping of acronym to expanded term described above. The string similarity and fuzzy-match screens can take parameters (e.g., similarity threshold), where string matches above that threshold are considered the generated candidates. These are defined in the flags as described above.

The match screen can be set to preprocess strings using various methods. For example, some of such methods can include punctuation removal: removing some, many, most, or all punctuation characters. For example, some of such methods can include whitespace removal: removing some, many, most, or all spaces and invisible characters from the string. For example, some of such methods can include parenthesis removal: removing some, many, most, or all parenthesis. For example, some of such methods can include lowercase conversion: converting some, many, most, or entire string to lowercase. For example, some of such methods can include uppercase conversion: converting some, many, most, or entire string to uppercase. For example, some of such methods can include token sort: sorting the terms in alphabetical order. For example, some of such methods can include stop word removal: removing common words. For example, some of such methods can include lemmatization. For example, some of such methods can include token culling based upon character length: truncating the terms at a fixed length (e.g., converting "types" and "typing" both to "typ"). For example, some of such methods can include general rule replacement (e.g., replace "tumor" with "neoplasm"). Note that same screen can be run multiple times sequentially with different string processing configurations. Further, note that various output ontology mentions from some, many, most, or all screens can be added to a candidates list.

An ontology mapping process for a single entity can include a candidate selection technique. Based upon various candidates generated, as explained above, the candidate selection technique can match an entity term to a most likely ontology candidate (or vice versa). First, the entity term is vectorized (see Example 2 below) using processing, as explained above, except that instead of processing tokens in a document, this can involve processing characters in a word. For example, using either/or the entity vector and the document ("context") vector, the entity mention can be matched to the ideal ontology candidate (or vice versa) via various processes. For example, some of such processes can include a deep learning classifier acting on the vectors. For example, some of such processes can include finding an ontology entry with a maximum distance via a cosine similarity measure. For example, some of such processes can include finding an ontology entry with a maximum distance via a machine-learning optimized non-Euclidean distance metric (e.g., pairwise learning to rank). As such, an output of this process can be a best-matched ontology entry and an overall weighting (confidence) of a match. If no match is found, then the output of this process can be set to a pre-determined null value or a corresponding informative message can be output (e.g., display, speaker).

An ontology mapping process for a single entity can include a false positive detection technique. A NER process and an ontology mapping process can try to map an entity mention into a fixed ontology (e.g., "COPD" into a MeSH disorder ontology). However, both the NER process and the ontology mapping process have a potential for a false positive, i.e., either a flagged entity mention or an ontology match that is not correct. As such, this functionality detects false positives and removes them (or flags them).

A false positive model can be a random forest or deep learning model that inputs various features. For example, some of such features include a confidence result, as described above. For example, some of such features include an entity frequency (e.g., number of times entity mentioned in document). For example, some of such features include a number of characters in an entity mention. For example, some of such features include a fraction of characters in an entity mention that are uppercase. For example, some of such features include a fraction of characters in an entity mention that are numbers. For example, some of such features include a number of words in an entity mention. For example, some of such features include a cosine distance between document embedding for a concept, as described above, and standard embedding for a concept, as described above. For example, some of such features include a set of Boolean flags marking whether a NER output is from a dictionary, a rules-based dictionary process, or a machine learning approach. Therefore, for some, many, most, or all ontology matches, some corresponding data features are run though the false positive model and a metric between 0 and 1 is calculated. If that metric is above a pre-defined false positive threshold, then an NER mention and an ontology match are rejected as false positives. If that metric is equal to or below the pre-defined false positive threshold, then the NER mention and the ontology match are not rejected as false positives. Note that these forms of threshold satisfaction can vary (e.g., rejection for being false positive when below false positive threshold, no rejection for being false positive when above false positive threshold).

Various methods for creating various machine learning models and various document vectors used in various candidate selections, as explained above, can include various components, as described below. For example, some of these components can include a document vectorizer, a character vectorizer, a vectorized ontology concept, a candidate selection model, or other components.

The document vectorizer can be created from via several methods. Some of such methods include TF-IDF, a machine learning-based approach (e.g., word2vec, doc2vec, fastText), or other methods. In order to create the vectorizer, a document pool can be created. The document pool can include (1) various data sources representative of various document types that contain relevant content to be used herein, (2) various data sources that are not representative of various document types to be used OR contain no relevant content, or (3) various annotations on some, many, most, or all documents that contain key concepts/topics. The vectorizer can be trained so that similarity between identical concepts is maximized while similarity between disparate concepts is minimized.

The character vectorizer can be trained for use in candidate selection, as explained above. As such, in order to train the character vectorizer used in the candidate selection, some, many, most, or all synonyms for some, many, most, or all concepts in a chosen ontology are pooled. Then, the concepts are split into a catalog of n-grams. Then, the n-grams are vectorized using TD-IDF (or another similar algorithm) on character clusters of lengths 3 through 6 characters (although these length can vary).

The vectorized ontology concepts can be based on a pool of documents that can be created, where the pool of documents can be representative of various types of text that needs to be curated. Some, many, most, or all documents in the pool are annotated (e.g. manually, automatically) with an ontology concept that is a primary topic in that document. Then, some, many, most, or all of the documents can be vectorized using the vectorizer, as explained above. Some, many, most, or all resulting vectors can be averaged by ontology concept to obtain representative vectors for those concepts.

The candidate selection model can be one among several models used herein. As such, in order to create some machine learning models, as described above, an initial pool of data can be created by annotating some datasets, as described above, with some raw ontology entity mentions and some corresponding ontology concepts found in those documents. This can form a mention-concept pairs used in model training. The entity mentions can be vectorized, as discussed above (e.g., candidate selection section). The entity mentions can be intentionally modified via adding/removing/changing characters or words to increase variation. The concept vectors created, as discussed above, and character vectors created, as discussed above, can be used as various concept definition vectors. In case of a classifier, a machine learning model can be trained using standard machine learning methods including a multi-class loss function (e.g., multi-class cross-entropy loss) and an optimizer (e.g., adaptive moment estimation (ADAM), stochastic gradient descent (SGD)). Some, many, most, or all incoming character and concept vectors can be concatenated and form an input and true ontology concepts can form detected classes. In case of a Non-Euclidean distance metric, a transformation matrix can be treated as a Pairwise-Learn-To-Rank problem. The transformation matrix can be trained using a multi-class Hinge loss or other standard pairwise ranking methods. A distance calculation can be a measure between a concatenated character and various concept vectors of various entity mentions and same vectors for an ontology concept.

Now that the several concepts have been described, the flowcharts of FIGS. 3A-B, 4A-4B can be described in light these several concepts. FIGS. 3A-3B show a process 300 having a plurality of sections 302-310. FIGS. 4A-4B show a process 400 having a plurality of sections 402-410. The process 300 and the process 400 different based on various types of ontology-specific screens used. In particular, the process 300 uses various screens inclusive of an acronym expansion screen and a lower case match screen both of which are activated, whereas the process 400 uses various screens inclusive of a lowercase match screen which is activated.

Regarding the process 300, the section 302 shows various data sources inclusive of a document 123 (e.g., Modern approaches to MI treatment in patients suggests that), a list of entities extracted from the document 123 (e.g., entity class: disorder, entity mention: MI, entity location: [20, 22], and a set of process configuration details, model definitions, and other process/model relevant data, as described herein.

The section 304 shows a candidate generation process involving the document 123 and an input mention string (e.g., MI) sourced from the list of entities. The document 123 undergoes a document vectorization process, as disclosed herein. The input mention string undergoes through various ontology-specific screens, where there are no matches and where there are matches. As shown, there is no exact match screen satisfaction. However, there is an acronym expansion screen satisfaction (e.g., Myocardial Infarction, Metapneumovirus Infection), which leads to a list of expanded mentions that is fed into a lowercase match screen, which generates a list of generated candidates (e.g., Mesh: D009209, Mesh: D029121, Mesh: D123456). Serially (before or after) or in parallel to ontology-screening, the input mention string undergoes an entity mention vectorization process, as disclosed herein.

The section 306 has the list of generated candidates, an output from the document vectorization process, and an output from the entity mention vectorization process being input into a machine-learning based candidate selection process, as disclosed herein. The machine-learning based candidate selection process identifies a selected candidate and generates a likelihood score for the selected candidate.

The section 308, the selected candidate and the likelihood score are processed via a true positive detection algorithm in order to determine if the selected candidate is a true positive (or not a false positive).

The section 310 has a decision tree. If the selected candidate is a true positive, then the list of entities extracted from the document 123 is modified (e.g., appended) with a name of ontology (e.g., MeSH), a concept identifier (e.g., D009203), a concept name (e.g., Myocardial Infarction), a weight (e.g., likelihood score, 0.85), and a true positive score (e.g., 0.91). However, if the selected candidate is not a true positive (false positive), then the list of entities extracted from the document 123 is modified to be blank or null.

Although the process 300 of FIGS. 3A, 3B is generally similar to the process 400B of FIGS. 4A, 4B, there are some differences. First, the input mention string is not a direct acronym. As such, some of the ontology-specific screens of section 404 (e.g., exact match screen, acronym expansion screen) are not activated until the lowercase match, which eventually results in the generated candidate. Second, the ontology used is not MeSH, but Entrez. Note that the process 300 and the process 400 are not limited to the ontology-specific screens shown in FIGS. 3A, 4A or described herein, but other ontology-specific screens known to skilled artisans can be used, whether additionally or alternatively. Likewise, the ontologies are not limited to the ontologies shown in FIGS. 3A, 3B, 4A, 4B or described herein, but other ontologies known to skilled artisans can be used, whether additionally or alternatively.

Example 1: Ontology Synonym List

This is an entry for a gene from the Entrez Gene Ontology. Items 1-11 are synonyms for the same gene. In this case the Gene Symbol is the preferred name for all of the synonyms.
Gene ID: 100507436
Gene Symbol: MICA
1. "MICA"
2. "truncated MHC class I polypeptide-related sequence A"
3. "MHC class I related chain A"
4. "MHC class I polypeptide-related sequence A"
5. "MHC class I chain-related protein A"
6. "stress inducible class I homolog"
7. "MHC class I related sequence A"
8. "HLA class I antigen"
9. "MICA"
10. "PERB11.1"
11. "MIC-A"

Example 2: A Document Vector

This lists first few terms of a document vector that can typically run into hundreds of thousands of terms. The phrase in quotes is the detected term and the number next to is the relative weight.
[('active', 4.2388334626278965),
('active site', 7.057614349562527),
('analysis', 2.6694633447940874),
('bile', 6.839612197748736),
('bile salt', 9.568496485753789),
('breast', 4.961748597624079),
('cdna', 6.8961643672536574),
('cdna library', 8.875349305193843),
('cholesterol', 5.765348938090913),
('clones', 7.10576369346011),
('conclusion', 4.653136284358119),
('confirmed', 4.203504722779899),
('covering', 6.5994324592811958),
('distinct', 4.68410093733214),
('domains', 5.398166016553765),
('encodes', 6.695824304957024),
('entire', 5.654370430128863),
('esterase', 8.684294068431134),
('highly', 3.956713886536513),
('homologous', 6.646467407986932),
('human', 3.34071241505171743),
('human breast', 7.600280579184177),
('human milk', 8.824056010806292),
('human pancreatic', 8.986574940304067),
('identical', 6.023730533594912),
('identity', 6.17257616111924765),
('including', 3.069422005992658),
('isolated', 4.436730937681203),
('isolated human', 8.902017552276003),
('isolation', 5.880933687524599),
('library', 5.951904799023656),
('lipase', 7.571293042310924),
('milk', 6.426160738007922),
('mrna', 4.854707938758877),
('nucleotide', 5.710540701595918),
('overlapping', 6.779594188022483),
('pancreas', 6.910816644040528),
('pancreatic', 5.904934839624142),
('peptide', 5.307300288509865),
('primary', 3.614706479319002),
. . . ]

Example 3: A Token Vector

This lists first few terms of a token vector that can typically run into hundreds of thousands of terms. The characters in quotes are detected from the tokens and the number next to is the relative weight.
[('ch', 4.931316729215325),
('cho', 7.733105771017902),
('chol', 8.468587315404408),
('chole', 9.645891872648182),
('es', 7.295352386532101),
('est', 8.124422733160038),
('este', 9.469435435306627),
('ester', 9.469435435306627),
('pa', 5.738440705673882),
('pan', 8.195881697142184),
('panc', 8.93535294937637),
('pancr', 9.025504046370665),
('anc', 5.630615833901775),
('ancr', 8.733116082881473),
('ancre', 8.909819647371204),
('ancrea', 8.909819647371204),
('ase', 3.491033778631765),
('ase', 3.6118384717827965),
('ati', 4.583318580869899),
('atic', 8.116789108304967),
('atic', 8.18361160455037),
('cho', 5.491955213223837),
('chol', 7.651072220560595),
('chole', 9.22303502182815),
('choles', 9.358209800196402),
('cre', 6.430530989887426),
('crea', 8.242205768816422), ('creat', 8.74730071787343),
('creati', 8.74730071787343),
('eat', 5.612427812930404),
('eati', 8.595192939675972),
('eatic', 9.189134470152468),
('eatic', 9.270102532686135),
('era', 4.45176611455299),
('eras', 4.980138345365448),
('erase', 4.9807990655744865),
('erase', 5.056637141965991),
('ero', 5.936607977180441),
('erol', 7.733105771017902),
('erol', 8.155553651755213),
('est', 5.681576072499403),
('este', 7.105533918323968),
('ester', 7.143593480148313),
('estera', 7.343306779654137),
('estero', 9.156343647329477),
('hol', 6.80548055406964),
('hole', 9.178083633965883),
('holes', 9.358209800196402), . . . ]

Example 4: Example Output of the Pass-All Candidate Screen

In this process, all ontology candidates are passed, regardless of input entity mention.
Input Entity Mention: "MICA"
Sample Ontology Concept List (key: synonym):
    100507436: "MICA"
    100507436: "truncated MHC class I polypeptide-related sequence A"
    100507436: "MHC class I related chain A"
    100507436: "MHC class I polypeptide-related sequence A"
    100507436: "MHC class I chain-related protein A"
    100507436: "stress inducible class I homolog"
    100507436: "MIC-A"
    142: "PARP1"
    142: "ARTD1"
    142: "poly(ADP-ribosyl)transferase"
    142: "pADPRT-1"
    142: "poly(ADP-ribose) synthetase"
    142: "poly[ADP-ribose] synthase 1"
    142: "poly(ADP-ribose) polymerase 1"
    . . . .
Output of Pass-All Candidate Screen:
    100507436: "MICA"
    100507436: "truncated MHC class I polypeptide-related sequence A"
    100507436: "MHC class I related chain A"
    100507436: "MHC class I polypeptide-related sequence A"
    100507436: "MHC class I chain-related protein A"
    100507436: "stress inducible class I homolog"
    100507436: "MIC-A"
    142: "PARP1"
    142: "ARTD1"
    142: "poly(ADP-ribosyl)transferase"
    142: "pADPRT-1"
    142: "poly(ADP-ribose) synthetase"
    142: "poly[ADP-ribose] synthase 1"
    142: "poly(ADP-ribose) polymerase 1"
    . . . .

Example 5: Example Output of Exact Match Candidate Screen

In this process, only strings that exactly match input entity (optionally ignoring punctuation and capitalization) are passed through.
Input Entity Mention: "MICA"
Sample Ontology Concept List (key: synonym):
    100507436: "MICA"
    100507436: "truncated MHC class I polypeptide-related sequence A"
    100507436: "MHC class I related chain A"
    100507436: "MHC class I polypeptide-related sequence A"
    100507436: "MHC class I chain-related protein A"
    100507436: "stress inducible class I homolog"
    100507436: "MIC-A"
    142: "PARP1"
    142: "ARTD1"
    142: "poly(ADP-ribosyl)transferase"
    142: "pADPRT-1"
    142: "poly(ADP-ribose) synthetase"
    142: "poly[ADP-ribose] synthase 1"
    142: "poly(ADP-ribose) polymerase 1"
    . . . .
Output of Exact Match Candidate Screen:
    100507436: "MICA"
    100507436: "MIC-A"

Example 6: Example Output of Partial Match Ontology Candidate Screen

In this process, only strings that contain input entity mention are passed forward.
Input Entity Mention: "polypeptide-related sequence A"
Sample Ontology Concept List (key: synonym):
    100507436: "MICA"
    100507436: "truncated MHC class I polypeptide-related sequence A"
    100507436: "MHC class I related chain A"
    100507436: "MHC class I polypeptide-related sequence A"
    100507436: "MHC class I chain-related protein A"
    100507436: "stress inducible class I homolog"
    100507436: "MIC-A"
    142: "PARP1"
    142: "ARTD1"
    142: "poly(ADP-ribosyl)transferase"
    142: "pADPRT-1"
    142: "poly(ADP-ribose) synthetase"
    142: "poly[ADP-ribose] synthase 1"
    142: "poly(ADP-ribose) polymerase 1"
    . . . .
Output of Partial Match Ontology Candidate Screen:
    100507436: "truncated MHC class I polypeptide-related sequence A"
    100507436: "MHC class I polypeptide-related sequence A"

Example 7: Example Output of Partial Match Entity Candidate Screen

In this process, only strings that are contained in input entity mention are passed forward.
Input Entity Mention: "serum MICA expression"
Sample Ontology Concept List (key: synonym):
    100507436: "MICA"

100507436: "truncated MHC class I polypeptide-related sequence A"
100507436: "MHC class I related chain A"
100507436: "MHC class I polypeptide-related sequence A"
100507436: "MHC class I chain-related protein A"
100507436: "stress inducible class I homolog"
100507436: "MIC-A"
142: "PARP1"
142: "ARTD1"
142: "poly(ADP-ribosyl)transferase"
142: "pADPRT-1"
142: "poly(ADP-ribose) synthetase"
142: "poly[ADP-ribose] synthase 1"
142: "poly(ADP-ribose) polymerase 1"
. . . .

Output of Partial Match Entity Candidate Screen:
100507436: "MICA"

Various embodiments of the present disclosure may be implemented in a data processing system suitable for storing and/or executing program code that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The present disclosure may be embodied in a system, a method, and/or a computer program product. The computer program product may include a computer readable storage medium (or media) having computer readable program instructions thereon for causing a processor to carry out aspects of the present disclosure. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a LAN or a WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions. The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

Features or functionality described with respect to certain example embodiments may be combined and sub-combined in and/or with various other example embodiments. Also, different aspects and/or elements of example embodiments, as disclosed herein, may be combined and sub-combined in a similar manner as well. Further, some example embodiments, whether individually and/or collectively, may be components of a larger system, wherein other procedures may take precedence over and/or otherwise modify their application. Additionally, a number of steps may be required before, after, and/or concurrently with example embodiments, as disclosed herein. Note that any and/or all methods and/or processes, at least as disclosed herein, can be at least partially performed via at least one entity or actor in any manner.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from the teachings of the present disclosure.

Furthermore, relative terms such as "below," "lower," "above," and "upper" can be used herein to describe one element's relationship to another element as illustrated in the accompanying drawings. Such relative terms are intended to encompass different orientations of illustrated technologies in addition to the orientation depicted in the accompanying drawings. For example, if a device in the accompanying drawings were turned over, then the elements described as being on the "lower" side of other elements would then be oriented on "upper" sides of the other elements. Similarly, if the device in one of the figures were turned over, elements described as "below" or "beneath" other elements would then be oriented "above" the other elements. Therefore, the example terms "below" and "lower" can encompass both an orientation of above and below.

Unless otherwise defined, all terms (including technical and scientific terms) used herein have the same meaning as commonly understood by one of ordinary skill in the art to which this disclosure belongs. The terms, such as those defined in commonly used dictionaries, should be interpreted as having a meaning that is consistent with their meaning in the context of the relevant art and should not be interpreted in an idealized and/or overly formal sense unless expressly so defined herein.

Although preferred embodiments have been depicted and described in detail herein, those skilled in the relevant art will appreciate that various modifications, additions, substitutions and the like can be made without departing from the spirit of the disclosure, and these are, therefore, considered to be within the scope of the disclosure, as defined in the following claims.

The invention claimed is:

1. A method comprising:
reading, via a processor, an acronym entity extracted from an unstructured text;
expanding, via the processor, the acronym entity such that a group of ontology candidate identifiers is generated;
vectorizing, via the processor, the unstructured text such that a first output is generated, wherein the first output includes a plurality of words and a plurality of first relative weights, wherein the first relative weights correspond to the words, wherein the unstructured text contains the words;
performing, via the processor, an entity mention vectorization on the acronym entity such that a second output is generated, wherein the second output includes a plurality of letter groups and a plurality of second relative weights, wherein the second relative weights correspond to the letter groups;
selecting, via the processor, a member of the group of ontology candidate identifiers based on the first words, the first relative weights, the letter groups, and the second relative weights;
generating, via the processor, a confidence score for the member;
determining, via the processor, whether the acronym entity is a false positive based on the first output, the second output, and the confidence score; and
writing, via the processor, the member and the confidence score into an index based on the acronym entity not being the false positive such that the member is associated with the confidence score in the index, wherein the index refers to the unstructured text based on the member.

2. The method of claim 1, wherein the acronym entity is extracted from the unstructured text via a named entity recognition process (NER).

3. The method of claim 1, wherein the acronym entity is expanded based on an ontology-specific dataset.

4. The method of claim 3, wherein the acronym entity is expanded based on the acronym entity matching an acronym in the ontology-specific dataset.

5. The method of claim 1, wherein the member of the group of candidate identifiers is selected based on at least one of a pattern or an inference learned from a dataset prior to the acronym entity being read.

6. The method of claim 1, wherein the group of candidate identifiers is sourced from at least one of a group of Medical Subject Heading (MeSH) identifiers, a group of Monarch Disease Ontology (MONDO) identifiers, a group of Disease Ontology (DO) identifiers, a group of Experimental Factor Ontology (EFO) identifiers, a group of INTERNATIONAL CLASSIFICATION OF DISEASES, NINTH EDITION (ICD9) identifiers, a group of INTERNATIONAL CLASSIFICATION OF DISEASES, TENTH EDITION (ICD10) identifiers, a group of Comparitive Toxicogenomics Database (CTD)'s MEDIC disease vocabulary identifiers, a group of SNOMED CT identifiers, a group of the National Center for Biotechnology Information (NCBI)'s Gene Entrez identifiers, a group of Ensembl Gene ID identifiers, a group of Uniprot identifiers, a group of Gene Ontology (GO) identifiers, a group of Protein Ontology identifiers, a group of HUGO GENE NOMENCLATURE COMMITTEE (HGNC)'S identifiers, a group of PFAM identifiers, a group of University of California Santa Cruz (UCSC) Genome identifiers, a group of Panther identifiers, a group of Kyoto Encyclopedia of Genes and Genomes (KEGG) identifiers, a group of National Center for Biotechnology Information (NCBI) Taxonomy identifiers, a group of Biological Assay Ontology (BAO) identifiers, a group of Human Phenotype Ontology (HPO) identifiers, a group of Mammalian Phenotype Ontology (MPO) identifiers, a group of ONLINE MENDELIAN INHERITANCE IN MAN(OMIM)'S identifiers, a group of Phenotype & Trait Ontology identifiers, a group of Cell Ontology (CL) identifiers, a group of Cell Line Ontology (CLO) identifiers, a group of Cellosaurus identifiers, a group of Gene Ontology (GO) identifiers, a group of Pathway Ontology identifiers, a group of Reactome identifiers, a group of Kyoto Encyclopedia of Genes and Genomes (KEGG)'s identifiers, a group of ConsensusPathDB identifiers, a group of ChemBL identifiers, a group of IUPAC identifiers, a group of ChEBI identifiers, a group of ChemINF identifiers, a group of FDA NATIONAL DRUG CODE (NDC) identifiers, a group of International Nonproprietary Name (INN) identifiers, a group of United States Adopted Name (USAN) identifiers, a group of Food and Drug Administration (FDA) Purple Book identifiers, a group of FDA Orange Book identifiers, a group of INTERNATIONAL UNION OF BIOCHEMISTRY AND MOLECULAR BIOLOGY (IUBMB) identifiers, a group of BRENDA identifiers, a group of dbSNP identifiers, a group of SNPedia identifiers, a group of THE AMERICAN MEDICAL ASSOCIATION'S CURRENT PROCEDURAL TERMINOLOGY(CPT) identifiers, a group of THE REGENSTRIEF INSTITUTE'S LOGICAL OBSERVATION IDENTIFIERS NAMES AND CODES (LOINC) identifiers, a group of Units of Measurement Ontology (UO) identifiers, a group of International Standards Organization (ISO) 3116-1 identifiers, a group of ISO 3116-2 identifiers, or a group of Geographic Entity Ontology (GEO) identifiers.

7. The method of claim 1, wherein the member of the group of candidate identifiers is a MeSH identifier.

8. The method of claim 1, wherein the processor runs a thread performing at least two of expanding the acronym entity, vectorizing the unstructured text, performing the entity mention vectorization, selecting the member of the group of candidate identifiers, generating the confidence score for the member, or writing the member and the confidence score into the index.

9. The method of claim 8, wherein the thread performing at least three of expanding the acronym entity, vectorising the unstructured text, performing the entity mention vectorization, selecting the member of the group of candidate identifiers, generating the confidence score for the member, or writing the member and the confidence score into the index.

10. The method of claim 9, wherein the thread performing at least four of expanding the acronym entity, vectorising the unstructured text, performing the entity mention vectorization, selecting the member of the group of candidate identifiers, generating the confidence score for the member, or writing the member and the confidence score into the index.

11. A method comprising:
reading, via a processor, a hyphenated entity extracted from an unstructured text;
performing, via the processor, a string match on the hyphenated entity such that an ontology candidate identifier is generated;
vectorizing, via the processor, the unstructured text such that a first output is generated, wherein the first output includes a plurality of words and a plurality of first relative weights, wherein the first relative weights correspond to the words, wherein the unstructured text contains the words;
performing, via the processor, an entity mention vectorization on the hyphenated entity such that a second output is generated, wherein the second output includes a plurality of letter groups and a plurality of second relative weights, wherein the second relative weights correspond to the letter groups;
selecting, via the processor, the ontology candidate identifier based on the first words, the first relative weights, the letter groups, and the second relative weights;
generating, via the processor, a confidence score for the ontology candidate identifier;
determining, via the processor, whether the hyphenated entity is a false positive based on the first output, the second output, and the confidence score; and
writing, via the processor, the ontology candidate identifier and the confidence score into an index based on the hyphenated entity not being the false positive such that the ontology candidate identifier is associated with the confidence score in the index, wherein the index refers to the unstructured text based on the ontology candidate identifier.

12. The method of claim 11, wherein the hyphenated entity is extracted from the unstructured text via a named entity recognition process (NER).

13. The method of claim 11, wherein the string match is performed on the hyphenated entity based on an ontology-specific dataset.

14. The method of claim 13, wherein the string match is performed on the hyphenated entity based on the hyphenated entity having a lowercase match in the ontology-specific dataset.

15. The method of claim 11, wherein the ontology candidate identifier is selected based on at least one of a pattern or an inference learned from a dataset prior to the hyphenated entity being read.

16. The method of claim 11, wherein the ontology candidate identifier is sourced from at least one of a group of Medical Subject Heading (MeSH) identifiers, a group of Monarch Disease Ontology (MONDO) identifiers, a group of Disease Ontology (DO) identifiers, a group of Experimental Factor Ontology (EFO) identifiers, a group of INTERNATIONAL CLASSIFICATION OF DISEASES, NINTH EDITION (ICD9) identifiers, a group of INTERNATIONAL CLASSIFICATION OF DISEASES, TENTH EDITION (ICD10) identifiers, a group of Comparitive Toxicogenomics Database (CTD)'s MEDIC disease vocabulary identifiers, a group of SNOMED CT identifiers, a group of the National Center for Biotechnology Information (NCBI)'s Gene Entrez identifiers, a group of Ensembl Gene ID identifiers, a group of Uniprot identifiers, a group of Gene Ontology (GO) identifiers, a group of Protein Ontology identifiers, a group of HUGO GENE NOMENCLATURE COMMITTEE (HGNC)'S identifiers, a group of PFAM identifiers, a group of University of California Santa Cruz (UCSC) Genome identifiers, a group of Panther identifiers, a group of Kyoto Encyclopedia of Genes and Genomes (KEGG) identifiers, a group of National Center for Biotechnology Information (NCBI) Taxonomy identifiers, a group of Biological Assay Ontology (BAO) identifiers, a group of Human Phenotype Ontology (HPO) identifiers, a group of Mammalian Phenotype Ontology (MPO) identifiers, a group of ONLINE MENDELIAN INHERITANCE IN MAN(O-MIM)'S identifiers, a group of Phenotype & Trait Ontology identifiers, a group of Cell Ontology (CL) identifiers, a group of Cell Line Ontology (CLO) identifiers, a group of Cellosaurus identifiers, a group of Gene Ontology (GO) identifiers, a group of Pathway Ontology identifiers, a group of Reactome identifiers, a group of Kyoto Encyclopedia of Genes and Genomes (KEGG)'s identifiers, a group of ConsensusPathDB identifiers, a group of ChemBL identifiers, a group of IUPAC identifiers, a group of ChEBI identifiers, a group of ChemINF identifiers, a group of FDA NATIONAL DRUG CODE (NDC) identifiers, a group of International Nonproprietary Name (INN) identifiers, a group of United States Adopted Name (USAN) identifiers, a group of Food and Drug Administration (FDA) Purple Book identifiers, a group of FDA Orange Book identifiers, a group of INTERNATIONAL UNION OF BIOCHEMISTRY AND MOLECULAR BIOLOGY (IUBMB) identifiers, a group of BRENDA identifiers, a group of dbSNP identifiers, a group of SNPedia identifiers, a group of THE AMERICAN MEDICAL ASSOCIATION'S CURRENT PROCEDURAL TERMINOLOGY(CPT) identifiers, a group of THE REGENSTRIEF INSTITUTE'S LOGICAL OBSERVATION IDENTIFIERS NAMES AND CODES (LOINC) identifiers, a group of Units of Measurement Ontology (UO) identifiers, a group of International Standards Organization (ISO) 3116-1 identifiers, a group of ISO 3116-2 identifiers, or a group of Geographic Entity Ontology (GEO) identifiers.

17. The method of claim 11, wherein the ontology candidate identifier is a MeSH identifier.

18. The method of claim 11, wherein the processor runs a thread performing at least two of performing the string match, vectorizing the unstructured text, performing the entity mention vectorization, selecting the ontology candidate identifier, generating the confidence score for the ontology candidate identifier, or writing the ontology candidate identifier and the confidence score into the index.

19. The method of claim 18, wherein the thread performing at least three of performing the string match, vectorizing the unstructured text, performing the entity mention vectorization, selecting the ontology candidate identifier, generating the confidence score for the ontology candidate identifier, or writing the ontology candidate identifier and the confidence score into the index.

20. The method of claim 19, wherein the thread performing at least four of performing the string match, vectorizing the unstructured text, performing the entity mention vectorization, selecting the ontology candidate identifier, generating the confidence score for the ontology candidate identifier, or writing the ontology candidate identifier and the confidence score into the index.

21. A method comprising:
reading, via a processor, an entity extracted from an unstructured text;
performing, via the processor, an ontology-specific screen on the entity such that an ontology candidate identifier is generated;
vectorizing, via the processor, the unstructured text such that a first output is generated, wherein the first output includes a plurality of words and a plurality of first relative weights, wherein the first relative weights correspond to the words, wherein the unstructured text contains the words;
performing, via the processor, an entity mention vectorization on the entity such that a second output is generated, wherein the second output includes a plurality of letter groups and a plurality of second relative weights, wherein the second relative weights correspond to the letter groups;
selecting, via the processor, the ontology candidate identifier based on the first words, the first relative weights, the letter groups, and the second relative weights;
generating, via the processor, a confidence score for the ontology candidate identifier;
determining, via the processor, whether the entity is a false positive based on the first output, the second output, and the confidence score; and
writing, via the processor, the ontology candidate identifier and the confidence score into an index based on the entity not being the false positive such that the ontology candidate identifier is associated with the confidence score in the index, wherein the index refers to the unstructured text based on the ontology candidate identifier.

22. The method of claim 21, wherein the ontology-specific screen at least one of
includes at least one of an exact match, an acronym expansion, or a lowercase match;
is the exact match;
is the acronym expansion;
is the lowercase match; or
is a first ontology-specific screen, wherein at least one of the exact match or the acronym expansion precede a second ontology-specific screen other than the lowercase match.

23. The method of claim 22, wherein the ontology-specific screen is a first ontology-specific screen, wherein the lowercase match precedes a second ontology-specific screen other than the exact match and the acronym expansion.

24. The method of claim 22, wherein the exact match precedes at least one of
the acronym expansion; or
the lowercase match.

25. The method of claim 22, wherein the acronym expansion at least one of
precedes the lowercase match;
occurs after the exact match and before the lowercase match;
immediately follows the exact match, wherein the lowercase match immediately follows the acronym expansion; or
precedes the second ontology-specific screen.

26. The method of claim 22, wherein the exact match precedes the second ontology-specific screen.

27. The method of claim 21, wherein the entity is an acronym entity, wherein the acronym entity is at least one of
- extracted from the unstructured text via a named entity recognition process (NER); or
- expanded based on an ontology-specific dataset.

28. The method of claim 27, wherein the acronym entity is expanded based on the acronym entity matching an acronym in the ontology-specific dataset.

29. The method of claim 21, wherein the entity is hyphenated entity and wherein the hyphenated entity is at least one of string matched such that the ontology candidate identifier is generated;
- extracted from the unstructured text via a named entity recognition process (NER);
- string matched based on an ontology-specific dataset;
- string matched based on the hyphenated entity having a lowercase match in the ontology-specific dataset.

30. The method of claim 21, wherein the entity includes at least one of
- a Greek letter; or
- a Roman numeral.

31. The method of claim 21, wherein the entity has a high token vector cosine similarity to an ontology concept, wherein the ontology candidate identifier and the ontology concept are associated with an ontology.

32. The method of claim 21, wherein the entity is at least two of an acronym entity, a hyphenated entity, an entity including a Greek letter, an entity that includes a Roman numeral, or an entity that has a high token vector cosine similarity to an ontology concept, wherein the ontology candidate identifier and the ontology concept are associated with an ontology.

33. The method of claim 21, wherein the entity is at least three of an acronym entity, a hyphenated entity, an entity including a Greek letter, an entity that includes a Roman numeral, or an entity that has a high token vector cosine similarity to an ontology concept, wherein the ontology candidate identifier and the ontology concept are associated with an ontology.

* * * * *